US00PP10215P

United States Patent [19]

Pieters

[11] Patent Number: Plant 10,215

[45] Date of Patent: Jan. 27, 1998

[54] CHRYSANTHEMUM PLANT NAMED 'DARK VERIA'

[76] Inventor: Dirk Pieters, Schierveldestraat 3A, Oosnieuwkerke, 8840 Staden, Belgium

[21] Appl. No.: 755,652

[22] Filed: Nov. 25, 1996

[51] Int. Cl.[6] ..... A01H 5/00

[52] U.S. Cl. ..... Plt./78

[58] Field of Search ..... Plt./78

[56] References Cited

U.S. PATENT DOCUMENTS

P.P. 802 7/1948 Prushek ..... Plt./78
P.P. 3,454 1/1974 Mack et al. ..... Plt./78
P.P. 5,661 2/1986 Meek et al. ..... Plt./78
P.P. 5,936 4/1987 Shoesmith ..... Plt./78
P.P. 6,404 11/1988 Mack et al. ..... Plt./78

*Primary Examiner*—Howard J. Locker
*Attorney, Agent, or Firm*—C. A. Whealy

[57] ABSTRACT

A distinct cultivar of Chrysanthemum plant named 'Dark Veria', characterized by its spherical and mounded plant habit; high vigor and moderate growth rate; decorative-type inflorescences with slight open center; bright yellow ray florets; numerous inflorescences per plant; and good garden performance.

2 Drawing Sheets

The present invention relates to a new and distinct cultivar of garden Chrysanthemum plant, botanically known as *Dendranthema grandiflora* and referred to by the cultivar name Dark Veria.

The new cultivar is a product of a planned breeding program conducted by the inventor in Staden, Belgium. The objective of the breeding program was to create new garden Chrysanthemum cultivars that are freely branching and have numerous and long-lasting inflorescences.

The new cultivar originated from a cross made by the inventor in 1988 of the nonpatented cultivar Veria as the female, or seed, parent with the nonpatented cultivar Quitpolin as the male, or pollen, parent.

The new Chrysanthemum was discovered and selected by the inventor as a flowering plant within the progeny of the stated cross in a controlled environment in Staden, Belgium.

Asexual reproduction of the new cultivar by terminal cuttings taken at Staden, Belgium, has shown that the unique features of this new Chrysanthemum are stable and reproduced true to type in successive generations.

The following traits have been repeatedly observed and are determined to be the unique characteristics of 'Dark Veria'. These characteristics in combination distinguish 'Dark Veria' as a new and distinct cultivar:

1. Spherical and mounded plant habit, vigorous, moderate growth rate, and freely branching.
2. Decorative-type inflorescences with slight open center.
3. Bright yellow ray florets.
4. Numerous inflorescences per plant.
5. Good garden performance.

The cultivar Dark Veria has not been observed under all possible environmental conditions. The phenotype may vary somewhat with variations in environment such as temperature, daylength and light intensity, without, however, any variance in genotype.

In side-by-side comparisons in Staden, Belgium, under commercial practice, plants of the new Chrysanthemum differ from plants of the female parent, the cultivar Veria, in ray floret color and vigor. In the same comparisons, plants of the new Chrysanthemum differ from the male parent, the cultivar Quitpolin, in ray floret color, foliage color, inflorescence size and vigor.

Plants of the new Chrysanthemum can be compared to the cultivar Yellow Triumph (U.S. Plant Pat. No. 7,955). However, in side-by-side comparisons conducted in Oxnard, Calif., under commercial practice, plants of the new Chrysanthemum differed from plants of the cultivar Yellow Triumph in the following characteristics:

1. Plants of the new Chrysanthemum are dense and spherical whereas plants of the cultivar Yellow Triumph are more open and not spherical.
2. Leaves of plants of the new Chrysanthemum have deeper sinuses and more pointed lobes compared to leaves of plants of the cultivar Yellow Triumph.
3. Plants of the new Chrysanthemum are more vigorous than plants of the cultivar Yellow Triumph.
4. Inflorescences of plants of the new Chrysanthemum are smaller but more numerous than inflorescences of plants of the cultivar Yellow Triumph.
5. Plants of the new Chrysanthemum have weaker and shorter peduncles than plants of the cultivar Yellow Triumph.

A detailed comparison of plants of the new Chrysanthemum and the cultivar Yellow Triumph appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Dark Veria' with five cuttings in the container.

The second photograph comprises a close-up view of five leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with night temperatures ranging between 14 and 20C., day temperatures ranging between 20 and 30C., and average light levels of 5,000 to 6,000 footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Dark Veria.

Commercial classification: Garden chrysanthemum.

Parentage:

*Female, or seed, parent.*—*Dendranthema grandiflora* cultivar Veria (not patented).

*Male, or pollen, parent.*—*Dendranthema grandiflora* cultivar Quitpolin (not patented).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Spherical and rounded growth habit. Moderate growth rate, vigorous and freely branching.

*Plant height.*—About 17 cm.

*Lateral branch length.*—About 13 cm.

*Quantity of lateral branches after removal of apical meristem.*—About 4 to 6.

*Stem color.*–143C.

*Foliage description.*—Number of leaves per plant: About 72. Number of leaves per lateral branch: About 12. Leaf arrangement: Alternate. Leaf size, fully expanded: Length: About 4.5 cm.—Width: About 3.4 cm. Leaf apex: Pointed, apiculate. Leaf base: Attenuate. Leaf margin: Palmately lobed with deep sinuses and pointed lobes. Leaf texture: Abaxial and adaxial surfaces slightly pubescent, smooth and dull. Veins prominent on abaxial surface. Petiole length: About 1.75 cm. Color: Young foliage adaxial surface: 146B. Young foliage abaxial surface: 147C. Fully expanded foliage adaxial surface: 147A. Fully expanded foliage abaxial surface: 147B. Venation adaxial surface: 147C. Venation abaxial surface: 147B. Petiole: 147C.

Inflorescence description:

*Appearance.*—Decorative-type inflorescence form with slight open center. Inflorescences borne on terminals above foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 49 days later. Inflorescences maintain good substance for three weeks under bright natural daylight.

*Quantity of inflorescences.*—About 5 to 7 inflorescences per flowering stem.

*Inflorescence size.*—Diameter: About 3.8 cm. Depth (height): About 1.4 cm. Diameter of disc: About 5 mm.

*Opening inflorescences.*—Bud shape: Spherical. Bud size: Length: About 7 mm. Width: About 6 mm. Bud color: 6A.

*Ray florets.*—Shape: Obovate. — Size: Length: About 1.7 cm. Width: About 7.5 mm. Apex: Blunt, tri- or quad-dentate. Base: Acute. Margin: Entire. Texture: Matte, smooth and glabrous. Aspect: Slightly upright. Number of ray florets per inflorescence: About 88. Color: When opening, adaxial surface: 9A. When opening, abaxial surface: 9C. Mature, adaxial surface: 9C. Mature, abaxial surface: 9D. Fading to: 10B.

*Disc florets.*—Shape: Tubular. Size: Length: About 4 mm. Width: About 1 mm.—Number of disc florets per inflorescence: About 32. Color: Immature: 154D. Mature: 154C.

*Peduncle.*—Aspect: Adequate, but somewhat weak, angled about 45° to the stem. Length: First peduncle: About 2 cm. Fourth peduncle: About 3.6 cm. Texture: Pubescent. Color: 138B.

*Reproductive organs.*—Androecium: Present on disc florets only. Anther color: 12A. Pollen: Moderate, 12A in color. Gynoecium: Present on both ray and disc florets. Style color: 154C.

Disease resistance: No known Chrysanthemum diseases observed to date on plants grown under commercial greenhouse conditions.

Seed production: Seed production has not been observed.

CHART A

| CHARACTERISTIC | 'DARK VERIA' | 'YELLOW TRIUMPH' |
|---|---|---|
| PLANT SHAPE | Spherical, rounded | Mounding |
| GROWTH HABIT | Short | Medium to short |
| GROWTH RATE/VIGOR | Moderate/ vigorous | Moderate/moderate |
| PLANT HEIGHT | About 17 cm | About 19 cm |
| LATERAL STEM LENGTH | About 13 cm | About 14 cm |
| QUANTITY OF LATERAL BRANCHES AFTER PINCHING | About 4 to 6 | About 3 to 4 |
| STEM COLOR | 143C | 146B |
| QUANTITY OF LEAVES PER LATERAL BRANCH | About 12 | About 15 |
| LEAF LENGTH | About 4.5 cm | About 5.3 cm |
| LEAF WIDTH | About 3.4 cm | About 3.8 cm |
| PETIOLE LENGTH | About 1.75 cm | About 2 cm |
| FOLIAGE LOCATION | Deep sinuses and pointed lobes | Not as deeply lobed |
| QUANTITY OF INFLORESCENCES PER LATERAL STEM | About 5 to 7 | About 4 to 6 |
| INFLORESCENCE FORM | Decorative with slight open center | Decorative, does not form open center until inflorescences are older |
| INFLORESCENCE DIAMETER | About 3.8 cm | About 5 cm |
| INFLORESCENCE HEIGHT | About 1.4 cm | About 1.6 cm |
| BUD COLOR | 6A | 7B |
| RAY FLORET SHAPE | Obovate | Spatulate |
| RAY FLORET TEXTURE | Matte | Velvety |
| RAY FLORET LENGTH | About 1.7 cm | About 2.3 cm |
| RAY FLORET WIDTH | About 7.5 cm | About 7 mm |
| RAY FLORET COLOR, WHEN OPENING, ADAXIAL | 9A | 9A |
| RAY FLORET COLOR, WHEN OPENING, ABAXIAL | 9C | 9B |
| RAY FLORET COLOR, MATURE, ADAXIAL | 9C | 7B |
| RAY FLORET COLOR, MATURE, ABAXIAL | 9D | 7D |
| RAY FLORET COLOR FADING TO | 10B | 7B |
| NUMBER OF RAY FLORETS PER INFLORESCENCE | About 88 | About 118 |
| DISC FLORET COLOR, IMMATURE | 154D | 154C |
| DISC FLORET COLOR, MATURE | 154C | 154C |

CHART A-continued

| CHARACTERISTIC | 'DARK VERIA' | 'YELLOW TRIUMPH' |
|---|---|---|
| NUMBER OF DISC FLORETS PER INFLORESCENCE | About 32 | About 18 |
| PEDUNCLE STRENGTH | Moderate | Strong |
| PEDUNCLE ANGLE | About 45° | About 30 to 35° |
| PEDUNCLE LENGTH, FIRST | About 2 cm | About 4.2 cm |
| PEDUNCLE LENGTH, FOURTH | About 3.6 cm | About 5 cm |

CHART A-continued

| CHARACTERISTIC | 'DARK VERIA' | 'YELLOW TRIUMPH' |
|---|---|---|
| PEDUNCLE COLOR | 138B | 146B |
| ANTHER COLOR | 12A | 14A |
| POLLEN COLOR | 12A | 14A |

It is claimed:

1. A new and distinct cultivar of Chrysanthemum plant named 'Dark Veria', as illustrated and described.

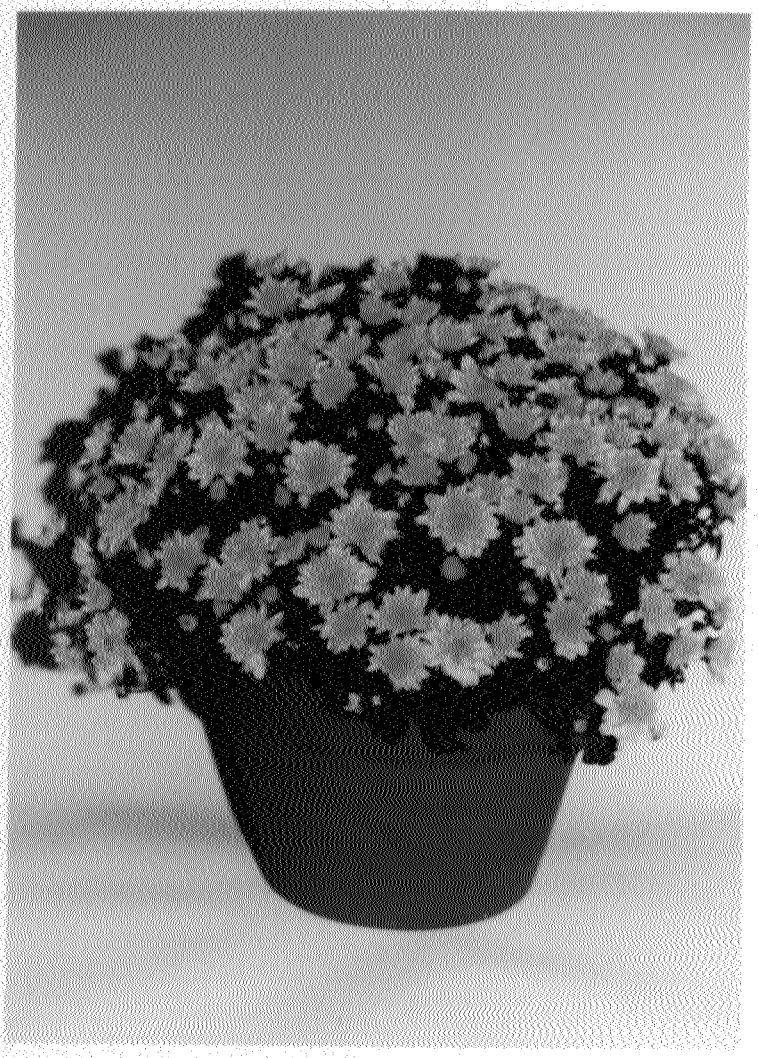

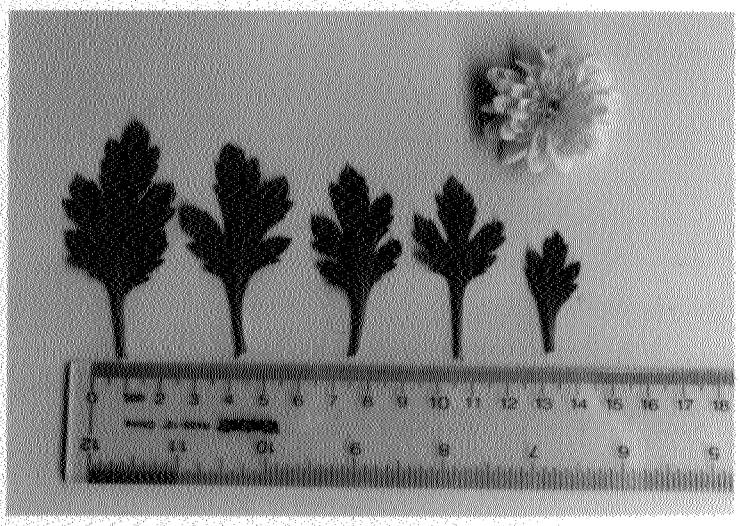

* * * * *